(12) United States Patent
Ririe

(10) Patent No.: US 10,413,905 B2
(45) Date of Patent: *Sep. 17, 2019

(54) THERMAL CYCLING SYSTEM AND METHOD OF USE

(71) Applicant: BioFire Defense, LLC, Salt Lake City, UT (US)

(72) Inventor: Kirk M. Ririe, Salt Lake City, UT (US)

(73) Assignee: BioFire Defense, LLC, Salt Lake City, UT (US)

( * ) Notice: Subject to any disclaimer, the term of this patent is extended or adjusted under 35 U.S.C. 154(b) by 124 days.

This patent is subject to a terminal disclaimer.

(21) Appl. No.: 15/408,717

(22) Filed: Jan. 18, 2017

(65) Prior Publication Data

US 2017/0165672 A1 Jun. 15, 2017

Related U.S. Application Data

(60) Continuation of application No. 13/936,137, filed on Jul. 5, 2013, now Pat. No. 9,586,208, which is a division of application No. 10/478,453, filed as application No. PCT/US02/22543 on Jul. 16, 2002, now abandoned.

(51) Int. Cl.
*C12Q 1/686* (2018.01)
*B01L 7/00* (2006.01)
*B01L 3/00* (2006.01)

(52) U.S. Cl.
CPC ............ *B01L 7/5255* (2013.01); *B01L 3/502* (2013.01); *B01L 3/505* (2013.01); *B01L 7/52* (2013.01); *B01L 7/525* (2013.01); *C12Q 1/686* (2013.01); *B01L 2300/0654* (2013.01); *B01L 2300/1822* (2013.01); *B01L 2300/1827* (2013.01); *B01L 2400/0481* (2013.01)

(58) Field of Classification Search
CPC ........ B01L 3/502; B01L 3/5025; B01L 3/505; B01L 7/52; B01L 7/525; B01L 7/5255; B01L 2400/0481; C12Q 1/686
See application file for complete search history.

(56) References Cited

U.S. PATENT DOCUMENTS

| | | | |
|---|---|---|---|
| 4,038,030 A * | 7/1977 | Albright ................ | B01L 3/545 356/246 |
| 6,780,617 B2 * | 8/2004 | Chen ..................... | B01L 3/5027 435/91.2 |
| 6,964,862 B2 * | 11/2005 | Chen ..................... | B01L 3/5027 435/91.2 |

(Continued)

*Primary Examiner* — William H. Beisner
(74) *Attorney, Agent, or Firm* — Maginot, Moore & Beck, LLP

(57) ABSTRACT

A temperature cycling system (10, 110) is provided for repeatedly heating and cooling a reaction mixture (16). The system (10, 110) includes a first heater (27) and a second heater (28) each movable between a first orientation in which the first or second heater (27, 28) affects the temperature of the reaction mixture (16) and a second orientation in which the first or second heater (27, 28) does not substantially affect the temperature of the reaction mixture (16). During temperature cycling, the second heater (28) is in the second orientation when the first heater (27) is in the first orientation, and the second heater (28) is in the first orientation when the first heater (27) is in the second orientation.

13 Claims, 9 Drawing Sheets

Specification includes a Sequence Listing.

(56) References Cited

U.S. PATENT DOCUMENTS

| | | | |
|---|---|---|---|
| 7,799,521 B2* | 9/2010 | Chen | B01L 3/502 |
| | | | 435/286.5 |
| 9,586,208 B2* | 3/2017 | Ririe | B01L 3/505 |
| 2002/0086417 A1* | 7/2002 | Chen | B01L 3/5027 |
| | | | 435/287.3 |

\* cited by examiner

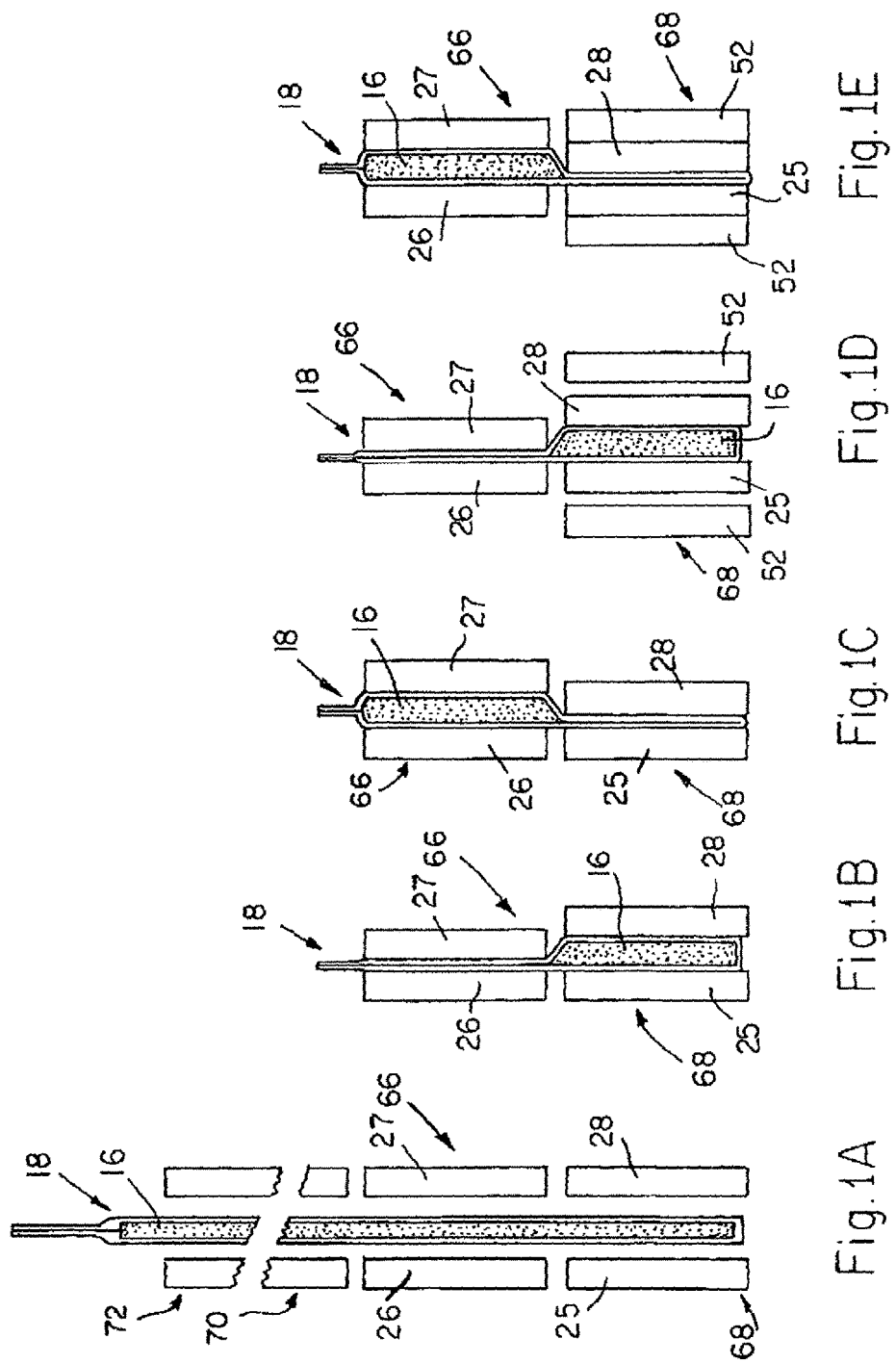

SEQUENCE LISTING

<160> NUMBER OF SEQ ID NOS: 2

<210> SEQ ID NO 1
<211> LENGTH: 20
<212> TYPE: DNA
<213> ORGANISM: Homo sapiens

<400> SEQUENCE: 1
acacaactgt gttcactagc         20

<210> SEQ ID NO 2
<211> LENGTH: 20
<212> TYPE: DNA
<213> ORGANISM: Homo sapiens

<400> SEQUENCE: 2
caacttcatc cacgttcacc         20

THERMAL CYCLING SYSTEM AND METHOD OF USE

PRIORITY CLAIM

This application is a continuation of and claims priority to co-pending U.S. application Ser. No. 13/936,137, filed on Jul. 5, 2013, which is a divisional application of and claims priority to U.S. application Ser. No. 10/478,453, filed on Nov. 21, 2003, now abandoned, which is a national stage entry under 35 U.S.C. § 371 of PCT/US2002/22543, filed on Jul. 16, 2002. The disclosures of each of the applications are incorporated herein by reference.

FIELD OF THE INVENTION

The present invention relates to a thermal cycling device and method that facilitates rapid, uniform temperature cycling of samples. Illustratively, the invention is designed to perform DNA amplification and detection of amplified products within a reaction vessel.

BACKGROUND

Amplification of DNA by polymerase chain reaction (PCR) requires reaction mixtures be subjected to repeated rounds of heating and cooling. All commercially available instruments for PCR operate by changing the temperature of the environment of a reaction vessel, either by heating and cooling the environment, or by robotically moving the samples between environments. The most common instruments for temperature cycling use a metal block to heat and cool reaction mixtures. Thermal mass of the metal block is typically large, meaning temperature transitions are relatively slow and require a large amount of energy to cycle the temperature. The reaction mixture is typically held in microcentrifuge tubes or microtiter plates consisting of rigid injection molded plastic vessels. These vessels need to be in uniform contact with the metal block for efficient heat transfer to occur. Maintaining temperature uniformity across a large heat block has also been a challenge.

Novel techniques have been devised to overcome the challenges of using instruments with metal blocks for heating and cooling samples. Airflow can be used to thermocycle samples in plastic reaction tubes (U.S. Pat. No. 5,187,084), as well as in capillary reaction tubes (Wittwer, et al, "Minimizing the time required for DNA amplification by efficient heat transfer to small samples", Anal Biochem 1990, 186: 328-331 and U.S. Pat. No. 5,455,175). Capillary tubes provide a higher surface area to volume ratio than other vessels. Using air as the thermal medium allows rapid and uniform temperature transitions when small sample volumes are used.

Further, the capillary tubes themselves can be physically moved back and forth across different temperature zones (Corbett, et al., U.S. Pat. No. 5,270,183, Kopp et al., 1998, and Haff et al., U.S. Pat. No. 5,827,480), or the sample can be moved within a stationary capillary (Hunicke-Smith, U.S. Pat. No. 5,985,651 and Haff, et al., U.S. Pat. No. 6,033,880). With the latter technique, contamination from sample to sample is a potential problem because different samples are sequentially passed through the winding capillary tube. Additionally, tracking the physical position of the sample is technically challenging.

The use of sample vessels formed in thin plastic sheets has also been described. Schober et al. describe methods for forming shallow concave wells on plastic sheets in an array format similar to a microtiter plate (Schober et al, "Multi-channel PCR and serial transfer machine as a future tool in evolutionary biotechnology", Biotechniques 1995, 18:652-661). After samples are placed in the pre-formed well, a second sheet is placed over the top, and the vessel is heat-sealed. The accompanying thermal cycling apparatus physically moves a tray of samples between different temperature zones (Schober et al. and Bigen et al., U.S. Pat. No. 5,430,957). The use of multiple heating blocks for the temperature zones makes this machine large and cumbersome.

Another system using reaction chambers formed between two thin sheets of plastic has been described where the vessel has multiple individual compartments containing various reaction reagents (Findlay et al, "Automated closed-vessel system for in vitro diagnostics based on polymerase chain reaction", Clin Chem 1993, 39:1927-1933, and Schnipelsky, et al., U.S. Pat. No. 5,229,297). The compartments are connected through small channels that are sealed at the beginning of the process. One apparatus has a moving roller that squeezes the vessel while traveling from one end of the vessel to another. The pressure from the roller breaks the seal of the channels and brings the sample into contact with reagents. Temperature is controlled by a heater attached to the roller mechanism (DeVaney, Jr., et al., U.S. Pat. No. 5,089,233). A second apparatus uses pistons to apply pressure to the compartments and move the fluid (DeVaney, Jr., U.S. Pat. No. 5,098,660). The temperature of one of the pistons can be altered while in contact with the vessel to accomplish thermal cycling. In both of these examples, the temperature of a single heating element is being cycled. Changing the temperature of the heating element is a relatively slow process.

Another system uses a planar plastic envelope (Corless et al. W09809728A1). The sample remains stationary and heating is provided by an infrared source, a gas laser.

Real-time monitoring of PCR is enabled using reaction chemistries that produce fluorescence as product accumulates in combination with instruments capable of monitoring the fluorescence. Real-time systems greatly reduce the amount of sample transfer required between amplification reaction and observation of results. Additionally, in some systems, quantitative data can also be collected.

A number of commercially available real-time PCR instruments exist that couple a thermal cycling device with a fluorescence monitoring system. Of these real-time instruments, thermal cycling in the Perkin-Elmer 5700 and 7700 and the Bio-Rad iCycler instruments are based on metal heat blocks. The Roche LightCycler, the Idaho Technology Ruggedized Advanced Pathogen Identification system (or R.A.P.I.D.) and the Corbett RotoGene all use air to thermocycle the reactions. The Cepheid SmartCycler uses ceramic heater plates that directly contact the sample vessel.

SUMMARY

The present invention provides a cycling system for use in various temperature-controlled processes, including but not limited to the polymerase chain reaction. The present invention also provides a new thermal cycling system capable of generally automatically and simultaneously varying the temperature of one or more samples. The present invention further provides a new thermal cycling system that allows a rapid and almost instantaneous change of temperatures between a plurality of temperatures by moving samples between temperature zones within each reaction vessel. Additionally the present invention provides a thermal cycling system for the detection and analysis of a reaction in real-time by monitoring cycle-dependent and/or temperature-dependent fluorescence.

In an illustrated embodiment, a reaction mixture is placed in a soft-sided flexible vessel that is in thermal contact with a plurality of temperature zones comprising a plurality of movable heating or heater elements. When pressure is applied to the vessel by closing all except one set of the heater elements, the reaction mixture inside the vessel moves to the heater element that is left open. The reaction mixture can be moved between different portions of the vessel and can be exposed to different temperature zones by selective opening and closing of the heater elements. Temperature change of the reaction mixture occurs rapidly and almost instantaneously. The vessel can be of any shape, illustratively elongated, and made of a flexible material, such as thin plastic film, foil, or soft composite material, provided that the material can hold the reaction mixture and can withstand temperature cycling. Exemplary plastic films include, but are not limited to, polyester, polyethylene terephthalate (PET), polycarbonate, polypropylene, polymethylmethacrylate, and alloys thereof and can be made by any process as known in the art including coextrusion, plasma deposition, and lamination. Plastics with aluminum lamination, or the like, may also be used.

A single vessel can be used for temperature cycling. Alternatively, for simultaneous temperature cycling, multiple vessels may be used simultaneously. The multiple vessels can be stacked together, as parallel channels in sheet format, or adjacent each other in a circle to form a disk. The heater elements can be made of, for example, thin-film metal heaters, ceramic semiconductor elements, peltier devices, or circuit boards etched with metallic (e.g. copper) wires, or a combination of the above, with optional metal plates for uniform heat dispersion. Thick metal heaters are also an option if the device need not be small. Other heaters known in the art may be used.

The heater elements are held at, or around, a set of characteristic temperatures for a particular chemical process, such as PCR. When the chemical process is PCR, at least two temperature zones are required: one at a temperature that is effective for denaturation of the nucleic acid sample, the other at a temperature that allows primer annealing and extension. As illustrated, reaction vessels are inserted in the apparatus when the heater elements for both temperature zones are in an open position. To temperature cycle for PCR, the heater element of one temperature zone is brought to the closed position, pushing the reaction mixture toward the open temperature zone at the other end of the vessel. In the open temperature zone, the heater element is in thermal contact with the vessel wall. Following an appropriate incubation time, the element of the zone heater is brought to the closed position, while the element of the other zone is opened. This action forces the reaction mixture to move to the other temperature zone. This process of opening and closing temperature zones is repeated as many times as required for nucleic acid amplification. It is understood that additional heater elements may be used for processes requiring more than two temperatures. For example, PCR reactions often use a denaturation temperature, an annealing temperature, and an extension temperature.

The foregoing and many other aspects of the present invention will become more apparent when the following detailed description of the preferred embodiments is read in conjunction with the various figures.

BRIEF DESCRIPTION OF DRAWINGS

FIGS. 1A to 1E are cross-sectional diagrammatic views of a reaction vessel containing a reaction mixture positioned between heater elements of the present disclosure.

FIG. 1A is a diagrammatic view of the vessel positioned between at least three pairs of heater elements showing each element spaced-apart from the vessel.

FIG. 1B is a diagrammatic view similar to FIG. 1A of the vessel positioned between two pairs of heater elements and showing a top pair of the elements in a closed position and a bottom pair of the elements in an opened position so that generally all of the reaction mixture is positioned between and heated by the bottom pair of elements.

FIG. 1C is a diagrammatic view similar to FIGS. 1A and 1B showing the bottom pair of elements in the closed position and the top pair of elements in the opened position so that generally all of the reaction mixture is positioned between and heated by the top pair of elements at a different temperature than the bottom pair of elements.

FIG. 1D is a diagrammatic view similar to FIG. 1B showing the bottom pair of elements in the opened position and the top pair of elements in the closed position and further showing a heat sink adjacent but spaced-apart from each of the bottom pair of elements.

FIG. 1E is a diagrammatic view similar to FIG. 1D showing the bottom pair of elements in the closed position and the top pair of elements in the opened position and further showing each of the heat sinks having engaged the respective element to cool the bottom pair of elements.

FIG. 4A is a side view thermocycling subassembly showing the top and bottom pairs of elements in the opened position prior to heating the reaction mixture within the vessels.

FIG. 4B is a side view of the thermocycling subassembly showing the bottom pair of elements in the closed position so that the reaction mixture is in thermal contact with the top pair of elements.

FIG. 4C is a side view of the thermocycling subassembly showing the top pair of elements in the closed position and the bottom pair of elements in the opened position so that so that the reaction mixture is in thermal contact with the bottom of elements.

DETAILED DESCRIPTION

Figure 5:
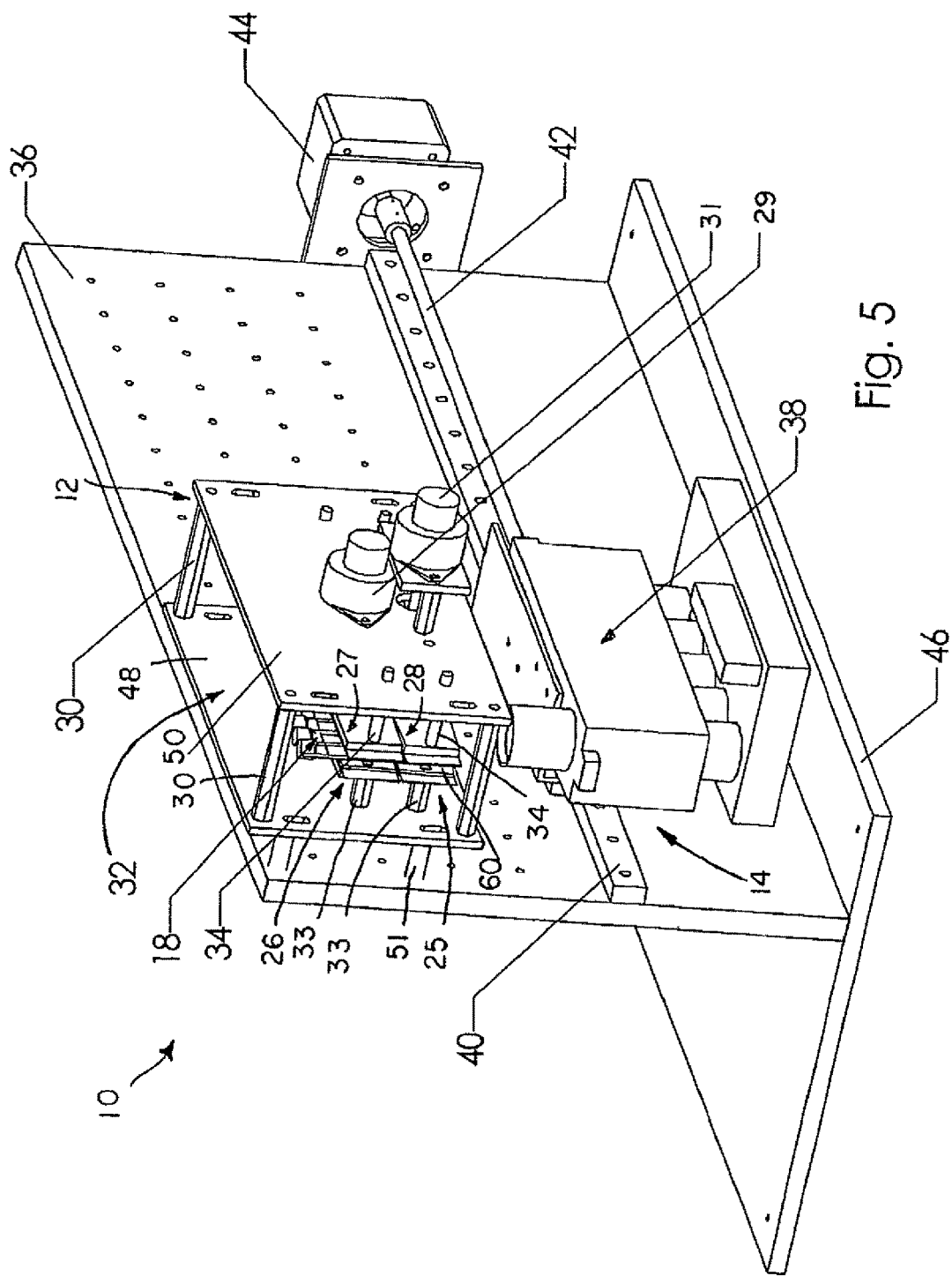
FIG. 5 is a perspective view of the thermocycling subassembly integrated into the real-time PCR apparatus including the thermocycling subassembly and a fluorimeter subassembly.
Figure 6:
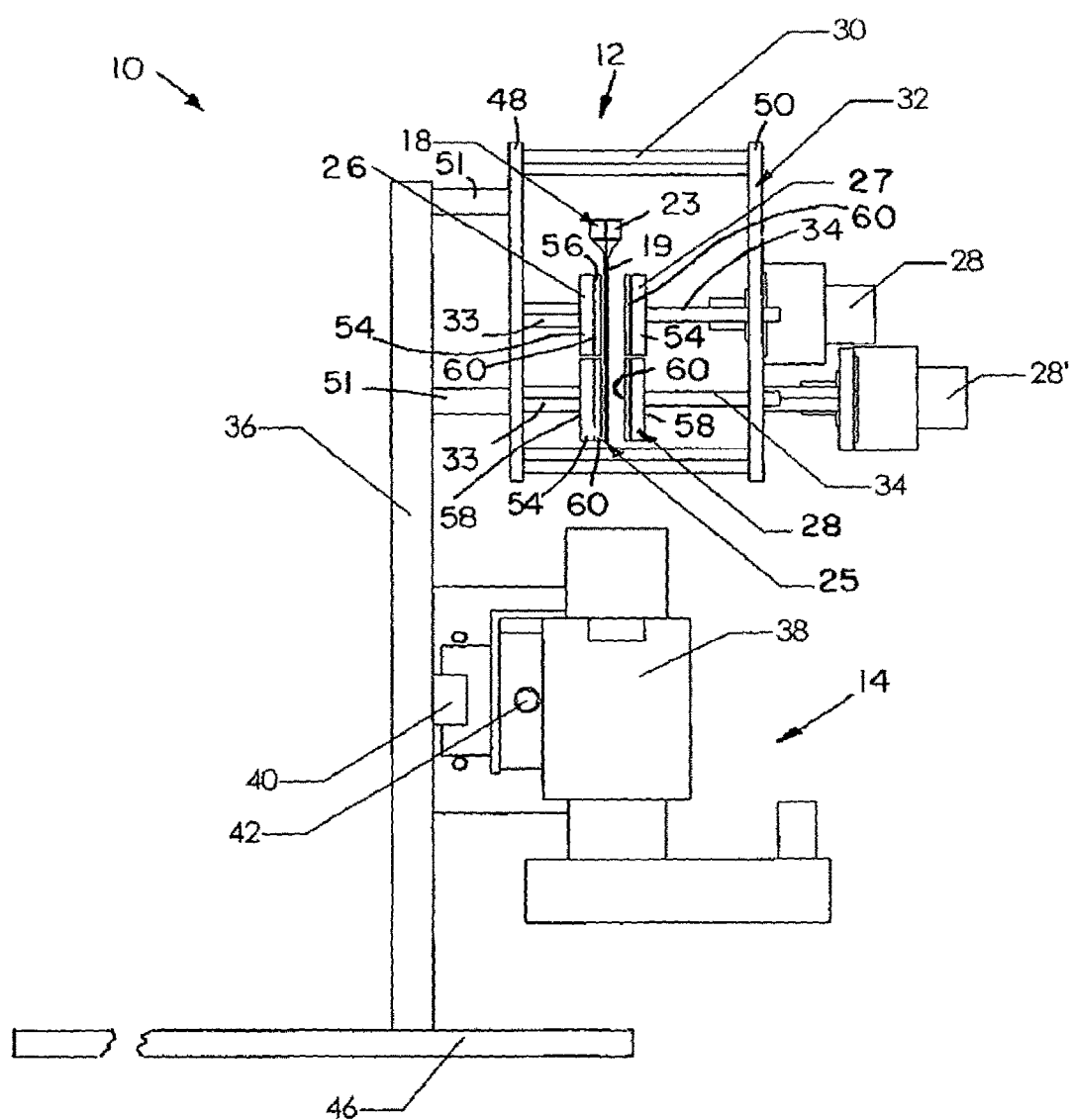
FIG. 6 is a side view of the real-time PCR apparatus shown in FIG. 5.

A real-time thermal cycling apparatus or system 10 is provided, as shown in FIGS. 5 and 6, for use in temperature controlled processes such as amplification of DNA by PCR or cycle-sequencing, for example, and optionally for use in detecting and analyzing a reaction by monitoring fluorescence. Illustratively, system 10 is used as a biological agent identification system for specifically identifying organisms by their unique genetic makeup. System 10 includes a thermocycling subassembly 12 and a fluorimeter subassembly 38. In general, thermocycling subassembly 12 subjects a reaction mixture or sample 16 (shown in FIGS. 1A-1E) including a nucleic acid sample to temperature cycling, or repeated rounds of heating and cooling, illustratively, for denaturation of the nucleic acid sample and for primer annealing and elongation. The samples 16 are sealed inside flexible plastic film vessels 18 and actuators of subassembly 12 squeeze the vessels 18 back and forth so that samples 16 are moved between two or more temperature zones. Subassembly 38 detects and analyzes the reaction in real-time by monitoring cycle dependent and/or temperature-dependent fluorescence. System 10 further includes a vertical support structure shown as mechanical breadboard 36 and a base 46 coupled to support structure 36. As is shown in FIG. 5, each subassembly 12, 38 is mounted on structure 36. Each of the subassemblies 12, 38 is discussed in greater detail below.

Figure 2A:
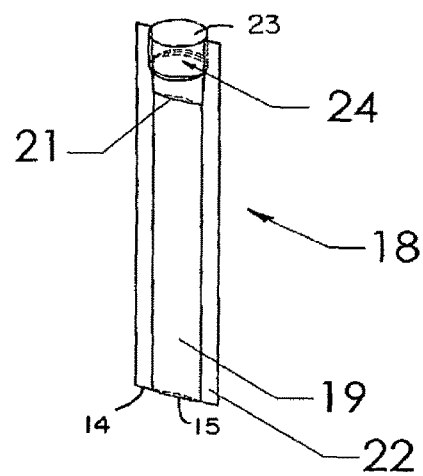
FIG. 2A is a perspective view of the reaction vessel showing a receptacle coupled to a flexible body of the vessel.

As mentioned above, reaction mixture 16 includes a nucleic acid sample, for example, and is contained within a single, soft-sided reaction vessel 18, as shown in FIG. 2A. Vessel 18 is used in system 10 and includes a reaction vessel body 19 and a receptacle 24 for receiving the nucleic acid sample 16. The reaction vessel body 19 is formed between two planar faces of plastic sheeting sealed together to form sealed sides 22. Individual vessels 18, therefore are separated from neighboring vessels 18 by sealed sides 22. Liquid can be loaded into the receptacle 24 and moved to the reaction vessel body 19, which is initially squeezed flat, by means such as gravity or a vacuum applied to the outer walls of the vessel 18. Once samples 16 are loaded into the reaction vessel body 19, the vessel 18 can be sealed to create seal 21 by heat-sealing, clamping, or through the use of adhesives, for example.

Alternatively, the receptacle 24 can be fitted with a plastic fitment (not shown) manufactured from polypropylene, for example. Each vessel body 19 may be tapered at the top to a point (not shown) with the plastic fitment coupled thereto so that through use of either a pipette or a syringe-like plug, samples 16 could be forced into the reaction vessel body 19. Each plastic fitment attaches to the top of a respective vessel body 19 and includes an injection port into the respective vessel body. Liquid reagents, therefore, may be injected into body 19 using a pipette, for example. Excess air may then be squeezed out of body 19 prior to loading the vessels 18 into the thermocycling subassembly 12 for heat-sealing and thermal cycling, as is described in greater detail below.

Additionally, an illustrative polypropylene fitting or plastic cap 23 (shown in FIGS. 2A and 2B) may be used to provide a secondary closure of the vessels 18. The plastic caps 23 may also be used to seal the vessel body 19 at the fitment, thereby obviating the need to seal body 19 at sealing area 21. It is within the scope of this disclosure for such a plastic cap 23 to be threadably attached to vessel body 19, snap-fit onto or within vessel body 19, and/or melted into body 19, etc.

Figure 10A:
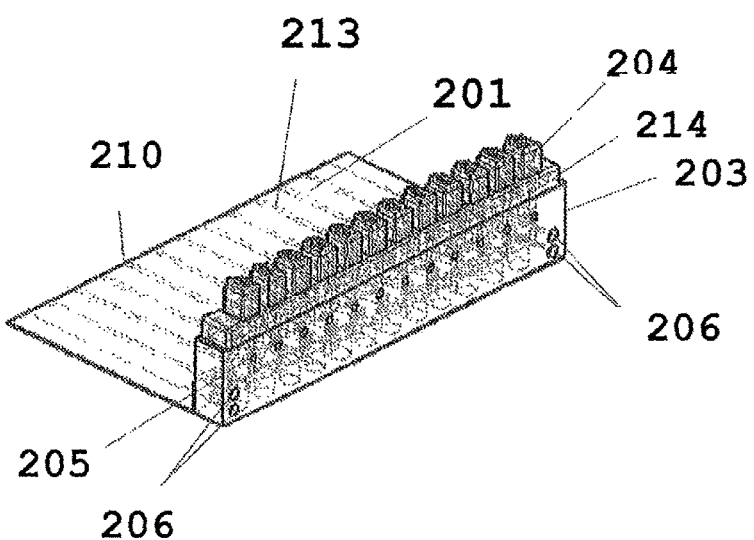
FIG. 10A is a perspective view of a twelve-compartment pouch assembly with a comb holding the plunger in position to adjust cavities to predetermined volumes.
Figure 10B:
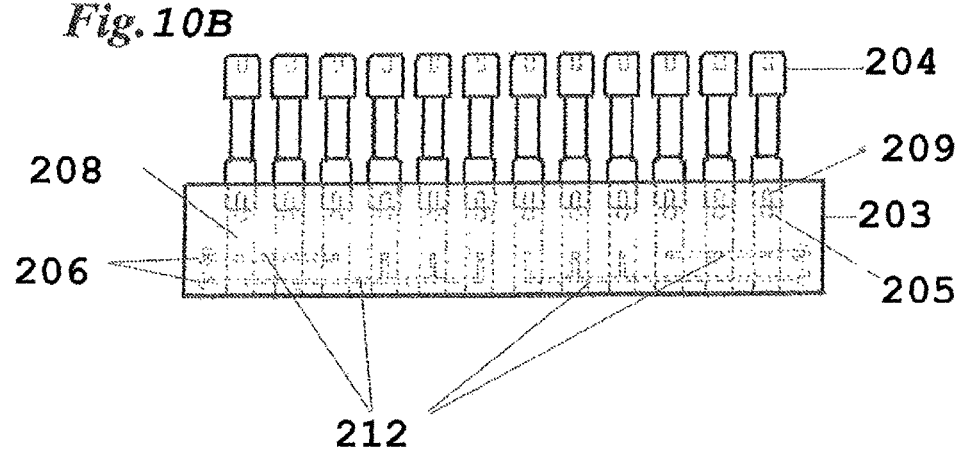
FIG. 10B is a back plan view of the fitment of the twelve-compartment pouch assembly at initial position prior to evacuation without the comb.

In yet another alternative embodiment, a larger plastic fitting or fitment may also be used to allow sample 16 to be freeze-dried inside a plurality of openings in the fitting, for example, twelve openings. A single injection port is connected to several of the reaction vessels 18, and when a prepared DNA sample is inserted into the port, the sample 16 is drawn into the body 19 of each vessel 18 automatically by the force of the vacuum. This automatic distribution of samples 16 may be used for testing sample 16 for multiple pathogens or multiple genes from a single source. A syringe plunger is inserted into the top of the fitting and is pressed down automatically at the end of the freeze-drying process, thus sealing the reagent pellet in vacuum. The body 19 is then vacuum sealed inside a protective bag for long-term stability. An illustrative twelve-compartment pouch assembly (FIGS. 10A-B) is constructed from polyethylene terephthalate-polypropylene laminates (0.48 mill PET/2 mill polypropylene-ethylene copolymer, Cello Pack, Buffalo, N.Y.) as barrier material, first by folding the barrier material on itself to fonl the bottom of the pouch 210, and then dividing the pouch into twelve compartments 201 by heat-sealed seams 213 coextensive with the length of the compartments 201. The top of the barrier material is sealed to one end of fitment 203 which is made of Monprene, a thermoplastic elastomer (MP 1627 1.3, QST Inc., St. Albans, Vt.). This provides one-to-one communication between compartments 201 and fitment cavities 208. In this fitment, there are four sample ports 206 each with seals (not shown), which if broken will connect each port 206 with three cavities 208 via branched channels 212. Inserted partially in said cavities 208 are plungers 204 made of solid polypropyrene with vacuum grease applied to the seal surface 211. The invention will be illustrated by means of dispensing three different liquids into nine equal-volume aliquots into the pouch compartments 201. After air is evacuated from the pouch assembly by use of a freeze-dryer (Virtis"Advantage," Cardiner, N.Y.) at a vacuum of 7 Pa., the volume of fitment cavities 208 is adjusted to 100 μl by lowering the plungers 204 that are then secured in position by a comb 214 (FIG. 10A). The pouch assembly is then taken out of the vacuum chamber. Four hundred microliters each of water, mineral oil, and PCR mixture are separately prepared inl-ml syringes. The PCR mixture comprises 0.2 mM dNTP, IX IT buffer (Idaho Technology, Cat #1770, Salt Lake City, Utah), 0.04 U/μl Taq polymerase, 500 pg/μl human genomic DNA, 0.5 μM each of primers PC03 and PC04 (LightCycler manual, p. 27, 1997, Idaho Technology), and 3×SYBR Green I dye. Cannulas attached to each syringe are used to puncture seals through ports 206, and the liquids are individually withdrawn by force of vacuum into three fitment cavities 208 that are in communication with channels 212. The diameter of channels 212 is kept at or smaller than 1 mm to minimize diffusion of fluid across cavities 208. The channels 212 are etched on the surface of fitment 203 and covered by barrier material. After the nine cavities are completely filled with liquid, the comb 214 is disengaged, and plungers 204 are twisted to seal access to channel 212, and then lowered to the bottom of cavity 208 to dispense the liquid into compartments 201. The microliter volume of liquid dispensed into each compartment 201 averaged 95.5±4.22. No appreciable difference was noted between the three samples, even though mineral oil has roughly 100 times higher viscosity than water or the PCR mixture. The pouch assembly was further inserted into an air thermal cycler (RapidCycler, Idaho Technology) with a modified lid so as to prevent escape of hot air from the chamber, and were exposed to 45 cycles of heating and cooling according to the referenced protocol (LightCycler manual, p 31). After thermal cycling, the pouch assembly was placed on a UV transilluminater. The three compartments that contained the PCR mixture, but not those that contained mineral oil or water, were found to have 3 to 4 times higher fluorescence intensity than before thermal cycling, indicating successful amplification of a gene fragment. Amplification of DNA was further confirmed by gel electrophoresis.

In another example using the twelve-compartment pouch assembly, PCR primers and dNTPs are dispensed into cavities 208 and freeze dried for 13 hours. A solution containing genomic DNA (500 pg/μl), buffer and Taq polymerase (0.04 U/μl) was prepared in a 1-ml syringe and dispensed into the pouch assembly as described above by puncture of seal through port 206 by a cannula. The force of vacuum distributed the solution equally into three fitment cavities 208. This operation was repeated four times so that all twelve cavities 208 were filled with solution. Then by twisting and lowering all of the plungers 204, the samples were transferred into the collapsible compartments 201. The pouch assembly was exposed to thermal cycling as described above, and all twelve reactions successfully produced amplified DNA products. See U.S. Provisional Application No. 60/374,730, filed Apr. 23, 2002, herein incorporated by reference.

Vessel body 19 is made of a flexible material. Such flexible materials include but are not limited to thin plastic films, foil, or soft composite materials, provided that they can hold the reaction mixture 16, and can withstand repeated exposure to temperatures used in the reaction without deformation, crazing, cracking, or melting. Plastic films of polyester, (PET), polycarbonate, polypropylene, polymethylmethacrylate, and alloys thereof made by coextrusion, plasma deposition, lamination or the like are preferred. Plastics with aluminum lamination, or the like, are also preferred. Further, vessel body 19 has a coefficient of heat transfer approximately in the range of 0.02-20 W/m*degK. Because vessel body 19 is thin, it does not effectively transfer heat between portions of vessel body 19 in contact with different heaters at different temperatures, as is discussed below.

If fluorescence monitoring of the reaction is desired, through the use of subassembly 38, for example, plastic films that are adequately low in absorbance and autofluorescence at the operative wavelengths are preferred. Such material could be found by trying different plastics, different plasticizers and composite ratios, as well as different thickness of the film. For plastics with aluminum or other foil lamination, the portion of the vessel 18 that is to be read by the fluorescence detection device 38 can be left without the foil. In the example of PCR, film laminates composed of polyester (Mylar, Dupont, Wilmington, Del.) of about 0.0048 inch (0.1219 mm) thick and polypropylene films of 0.001-0.003 inch (0.025-0.076 mm) thick perform well. Illustratively, vessel body 19 is made of a clear material so that the vessel body 19 is capable of transmitting approximately 80%-90% of incident light.

Figure 2B:
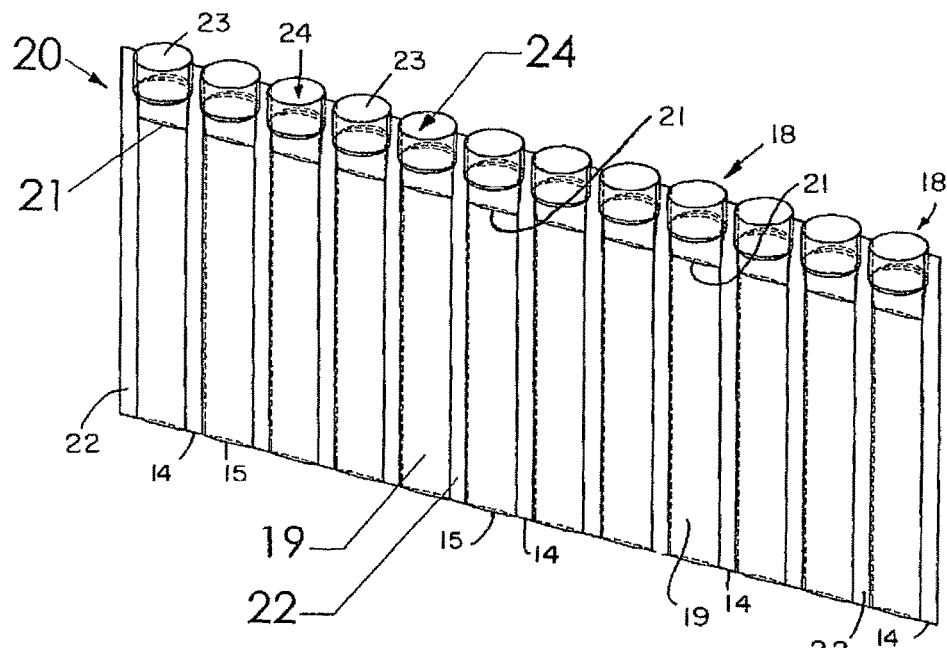
FIG. 2B is a perspective view of an array of reaction vessels coupled to each other to form a single row.

To perform simultaneous reactions of multiple samples, the vessels 18 are illustratively arranged to form an array or row 20 of reaction vessels 18, as shown in FIG. 2B. In the illustrated embodiments, the vessels 18 are arranged with 9 mm or 6 mm spacing to mimic the spacing found on standard 96-well or 384-well microtiter plates. However, it is within the scope of this disclosure to include a row 20 of vessels 18 having other suitable spacing. FIG. 2B illustrates the row or array 20 of vessels 18 to includes twelve reaction vessels 18. It is within the scope of this disclosure, however, to include other configurations having other numbers of vessels 18 for use with system 10 of the present disclosure. When used with fluorescence, for example, for real-time monitoring, a bottom edge 14 of sealed sides 22 may be blackened to reduce bleed-over of fluorescent light from one sample vessel 18 to the next.

Figure 3:
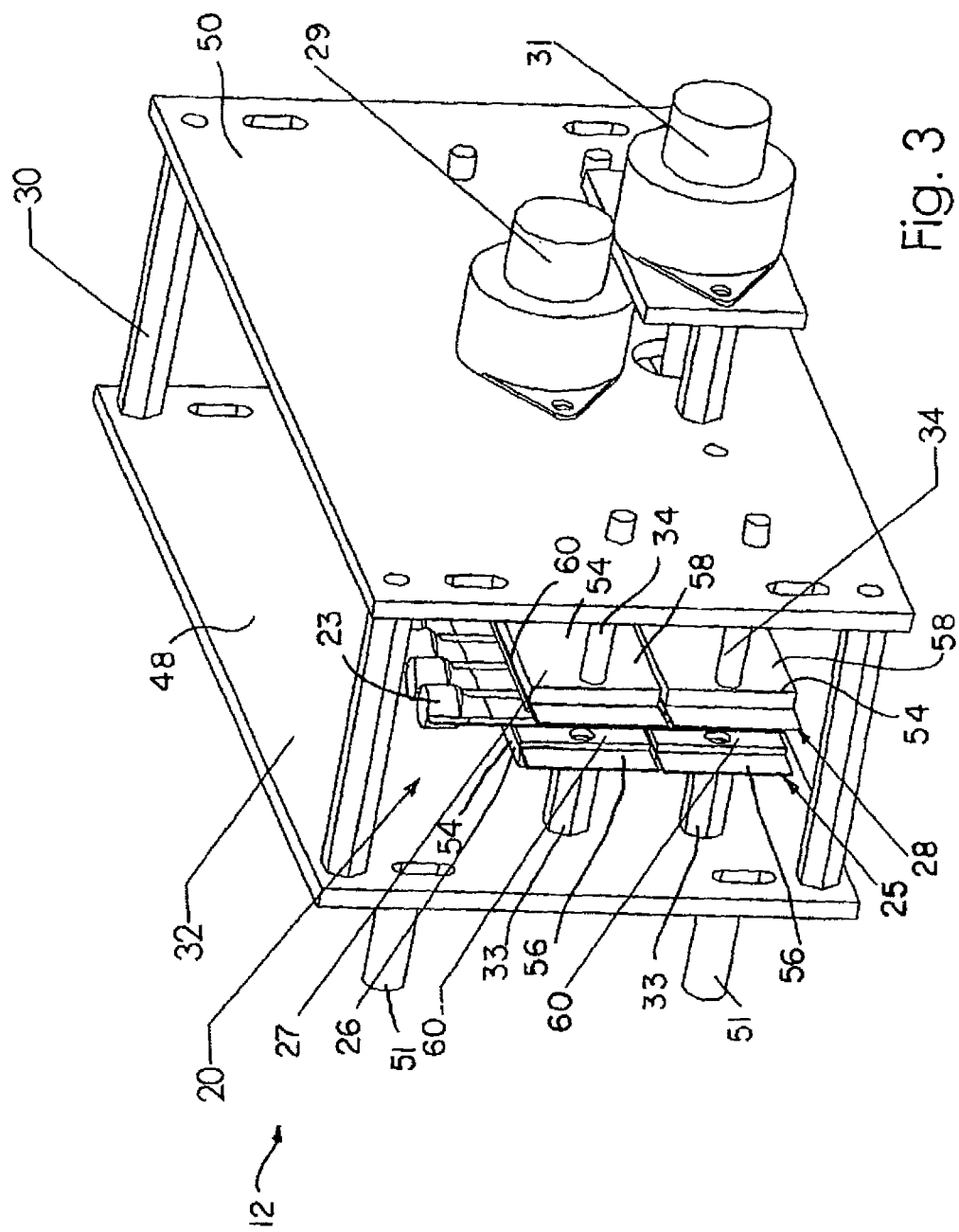
FIG. 3 is a perspective view of an illustrative thermocycling subassembly for use with a real-time PCR apparatus of the present disclosure (shown in FIGS. 5 and 6) showing a first and a second stepper motor of the subassembly, top and bottom pairs of heater elements, and the row of reaction vessels positioned between the pairs of elements.

As mentioned above, vessels 18 (or row 20 of vessels 18) are used with thermocycling subassembly 12, shown in FIGS. 3-5. Illustratively, as shown in FIG. 3, thermocycling subassembly 12 includes a mounting support 32 having a first wall 48 and a second wall 50 spaced apart from first wall 48 and coupled to first wall 48 by spacers 30. Illustratively, there are four spacers 30 coupled to each of the first and second walls 48, 50 of support 32. Mounting support 32 further includes mounts 51 coupled to first wall 48 so that mounting support 32 may be coupled to support structure 36, as shown in FIG. 6, for example.

Illustratively, thermocycler subassembly 12 further includes four heaters: a first heater 25, a second heater 26, a third heater 27, and a fourth heater 28, as shown in FIG. 3 and as shown diagrammatically in FIGS. 1A-1E. Each heater 25, 26, 27, 28 includes a head 54 having a first surface 56 facing the one or more vessels 18, as is discussed below, and an opposite surface 58. Illustratively, each head 54 is generally rectangular in shape, as shown in FIG. 3. However, it is within the scope of this disclosure to include a head having any suitable shape for thermally contacting vessels 18.

Each heater 25, 26, 27, 28 further includes a heater element 60 coupled to the contact surface 56 of each heater 25, 26, 27, 28. Heater element 60 illustratively may be a thin-film metal heater or one or more circuit-board based heaters, or a combination of the two. Metallic (e.g. copper) wires or traces may be etched into the circuit-board based heaters. Each heater head 56 is illustratively a metal plate so that heat produced by heater elements 60 may be uniformly dispersed or distributed. Each head or metal plate 56, however, is an optional component of the heaters 25, 26, 27, 28. Circuit-board based heater elements provide heating by controlling the voltage across the metallic traces and provide temperature sensing by measuring the resistance of the metallic traces. It is within the scope of this disclosure, however, to include other types of temperature sensors. A microprocessor can be used to read the calibrated temperature of the circuit-board and control the voltage to achieve the desired temperature. It is also within the scope of this disclosure to include an outer un-etched copper layer of each heater element 60 to increase temperature uniformity. Thick metal heaters and Peltier devices are also an option if the device need not be small. Optional active heating can be performed at the higher temperature zone(s) by applying heat purges, or the like, prior to or during sample contact. Optional active cooling could be used at the lower temperature zone(s) by use of heat sinks 52 or the like, which are to be in contact with the heating elements (shown in FIGS. 1D and 1E) for appropriate durations of time, as is discussed below.

Figure 4A:
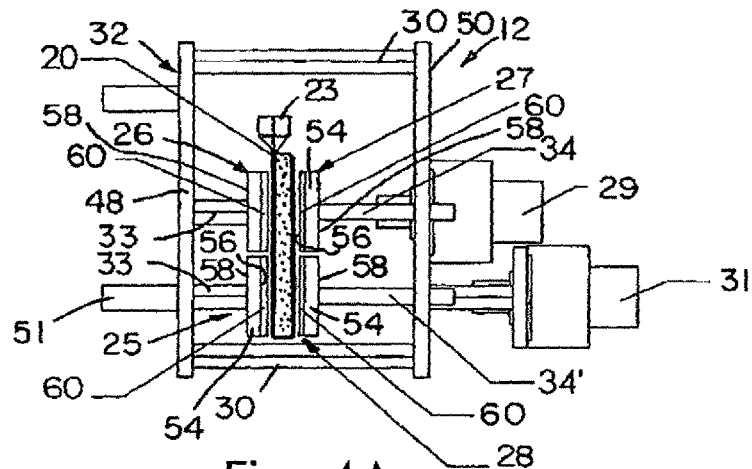
FIGS. 4A to 4C are side views of the thermocycling subassembly shown in FIG. 3 showing thermocycling of the reaction mixture contained within the vessels.
Figure 4B:
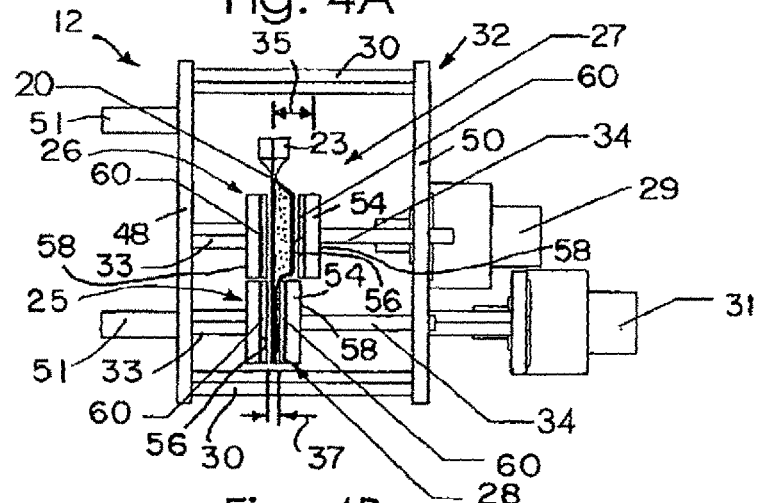
Figure 4C:
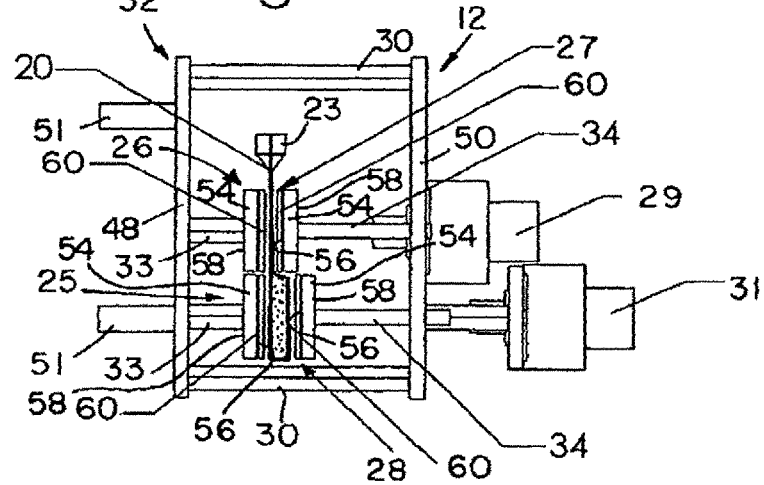

As shown in FIG. 3, and diagrammatically in FIGS. 1A-1E, each of the first and second heaters 25, 26 is rigidly coupled to first wall 48 of mounting support 32 by a shaft 33. Each shaft 33 is rigidly coupled to first wall 48 so that first and second heaters 25, 26 remain stationary throughout the temperature cycling process, as is described below. Each of the second and third heaters 27, 28 are movably coupled to second wall 50 of mounting support 32 by a shaft or linear bearing 34. As shown in FIGS. 4A-4C, each shaft 34 is rigidly coupled to respective heaters 27, 28 so that heaters 27, 28 are urged to move with each respective shaft 34 relative to wall 50.

Further, second and third heaters 26, 27 create a first, upper temperature zone 66 and first and fourth heaters 25, 28 create a second, lower temperature zone 68. Illustratively, the upper zone 66 is provided for denaturation of the sample 16 while the lower zone 68 is provided for primer annealing and extension. The heaters of each zone 66, 68 are programmed to maintain a certain predefined temperature for the heating and cooling of mixture 16 within each vessel 18. As such, zone 66 (including second and third heaters 26, 27) is maintained at a different temperature than zone 68 (including first and fourth heaters 25, 28). The upper and lower zones 66, 68 of heaters are diagrammatically shown in FIGS. 1A-1E, for example, and are discussed in greater detail below. Further, it is within the scope of this disclosure to include a thermocycling subassembly 12 having additional temperature zones (and thus more heaters) than upper and lower zones 66, 68 described herein. For example, third and fourth temperature zones 70, 72 are illustratively shown in FIG. 1A.

Thermocycler subassembly 12 further includes a first stepper motor 29 and a second stepper motor 31, as shown in FIG. 3. First stepper motor 29 is coupled to and controls third heater 27 positioned in the first, upper zone 66. Second stepper motor 31 is coupled to and controls fourth heater 28 positioned in the second, lower zone 68. Each stepper motor 29, 31 is provided to move the respective heaters 27, 28 in a linear path along an axis lying along the length of shafts 34. Although stepper motors 29, 31 are shown, it is within the scope of this disclosure to include any suitable type of electromechanical mover or actuator such as servo motors, geared motors, solenoids, piezo-electric devices, etc., for example.

FIG. 1A diagrammatically illustrates a single soft-sided reaction vessel 18 sandwiched between heaters 25, 26, 27, 28 for use with system 10, and specifically with subassembly 12, of the present disclosure. As mentioned above, the heaters create two or more temperature zones: first, upper zone 66 and second, lower zone 68. Each of the third and fourth heaters 27, 28 is movable between an opened and a closed position because of respective stepper motors 29, 31. As shown in FIG. 1A, all sets of heaters are illustratively in an open position for ease in loading vessels 18 therein. As described below and shown in FIGS. 1B-1E, the reaction mixture 16 inside the reaction vessel 18 is incubated in a particular temperature zone when the particular heater within that temperature zone is held in the opened position while all other heaters within other zones are in the closed position. FIG. 1B illustrates an exemplary two-temperature cycling system in which the third heater 27, within upper temperature zone 66, is in the closed position. As shown in FIG. 1B, the portion of vessel 18 within zone 66 has been pressed together to squeeze substantially all of reaction mixture 16 into the portion of vessel 18 within zone 68 (where heater 28 is in the opened position). Therefore, the reaction mixture 16 is in full thermal contact with first and fourth heaters 25, 28 within zone 68 to be heated and/or cooled to the temperature at which first and fourth heaters 25, 28 have been set. Conversely, since reaction mixture 16 has been squeezed from zone 66 into zone 68, little, if any, reaction mixture 16 remains at the temperature of zone 66.

After an appropriate duration, heater 27 is moved to the open position so that zone 66 is opened and heater 28 is moved to the closed position so that zone 68 is closed, thus moving the reaction mixture 16 into the upper portion of vessel 18 and into full thermal contact with second and third heaters 26, 27 of upper zone 66, as shown in FIG. 1C. Thermal cycling is accomplished by repeating these steps. It is within the scope of this disclosure for approximately 90% or more of the reaction mixture 16 to be transferred between upper and lower temperature zones 66, 68. However, it is within the scope of this disclosure for subassembly 12 to achieve other suitable amounts of mass transfers of mixture 16 during the thermal cycling process. For a two-temperature cycling system, as that shown in FIGS. 1B-1E, the volume of reaction mixture 16 to be placed within each vessel 18 is approximately less than half the maximum volume of the reaction vessel body 19 at any time so that all or substantially all of reaction mixture 16 can be moved between the two temperature zones 66, 68.

FIGS. 1D and 1E illustrate the use of optional heat sinks 52 to aid with the active cooling of the heaters 25, 28 in the lower temperature zone 68. Illustratively, heat sinks 52 are provided for use with heaters 25, 28 of the lower temperature zone 68 for active cooling of heaters 25, 28 during the denaturation phase of the PCR process, as shown in FIG. 1E. Alternatively, heat sinks 52 are used for active cooling of heaters 25, 28 during the annealing/extension phase (not shown), or are used continuously by being affixed directly to heaters 25, 28 (not shown). Illustratively, heat sinks 52 are aluminum or copper. However, it is within the scope of this disclosure to include other heat sinks made of other suitable materials. The lower temperature zone 68 is actively cooled by bringing heat sinks 52 into contact with the back-side or surface 58 of heaters 25, 28. During the denaturation phase, the top portions of heaters 25, 28 in the lower temperature zone 68 may have a higher temperature than the remaining portions due to proximity to the higher temperature zone 66 and due to contact with the lower end of the heated fluid sample 16 through the vessel material. Unevenness in temperature along the length of heaters 25, 28 can lead to inefficient and uneven cooling of the sample 16 when the sample 16 is transferred into the lower temperature zone 68 for annealing/extension. When heat sinks 52 are used during the denaturation phase, they generally circumvent this problem by preventing the occurrence of non-uniform temperature in the lower temperature zone 68. When heat sinks 52 are used during the annealing/extension phase, they aid in regaining temperature uniformity in the lower temperature zone 68 and allow for a more rapid cool down of the denatured sample when it is transferred into the lower temperature zone 68. When heat sinks 52 are affixed to heaters 25, 28, they help maintain temperature uniformity of the heaters, and allow for rapid cool down of the denatured sample. By selecting the appropriate thermal mass for the affixed heat sinks 52, it is also possible to minimize power consumption by heaters 25, 28.

Illustratively, subassembly 12 features an active area between the heaters 110 mm wide and 50 mm high. This is large enough to accommodate twelve reaction vessels 18 (such as array 20) of 100 µl, or 9 mm of spacing. However, it is within the scope of this disclosure to include a device having another suitably sized active area for vessels 18.

FIG. 3 illustrates an exemplary subassembly 12 of the system 10 of the present disclosure. The parallel array or row 20 of reaction vessels 18 is shown and positioned between first and second heaters 25, 26 and third and fourth heaters 27, 28. For illustrative PCR applications, second and third heaters 26, 27 are maintained at a first temperature high enough to denature double-stranded DNA, typically 90 to 96 degrees Celsius. First and fourth heaters 25, 28 are maintained at a second temperature, between 50 and 72 degrees Celsius, to allow annealing of probe, and extension by a thermostable DNA polymerase. It is within the scope of this disclosure for both of these temperatures to be predetermined, or to be dynamically determined through fluorescence feedback if fluorescence monitoring is performed in real-time using dye systems that discriminate double strand from single strand DNA. See U.S. Pat. No. 6,174,670, for example.

Figure 9:
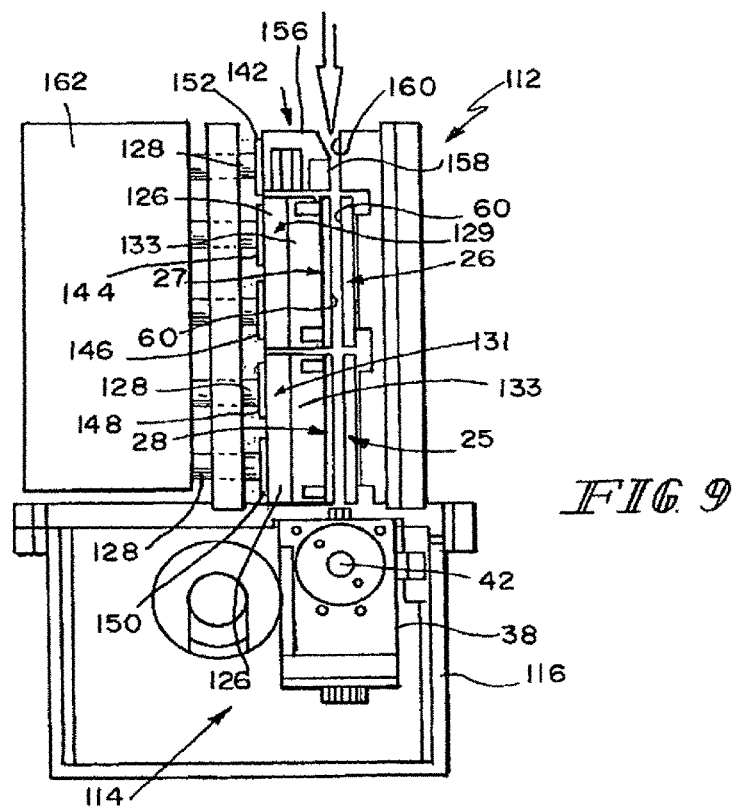
FIG. 9 is a part schematic, part diagrammatic sectional view of the components located within the body of the PCR apparatus shown in FIG. 8 showing an alternative thermocycling subassembly having pneumatic bladders and the fluorimeter subassembly positioned below the thermocycling subassembly.

As shown in FIG. 4A, the mobile or movable third and fourth heaters 27, 28 are each mounted on respective shaft 34. The stepper motor 29 acts to adjust the distance between the third heater 27 and the stationary second heater 26 by propelling the mobile third heater 27 with the shaft 34 in a direction toward stationary heater 26. In the same manner, the distance between the heaters in the lower zone 68 (defined by first, stationary heater 25 and fourth, movable heater 28) is controlled by second stepper motor 31. Means to control the opening and closing of temperature zones 66, 68 do not have to be limited to stepper motors. For instance, the use of pneumatic bladders, as shown in FIG. 9, to move the third and fourth heaters 27, 28 is also a viable method. It is, therefore, within the scope of this disclosure to include other suitable means of moving heaters 25, 26, 27, 28 toward and away from each other. Further, it is within the scope of this disclosure to move both sets of heaters within a particular zone. Furthermore, as best seen in FIG. 3, each heater 25, 26, 27, 28 is elongated and shaped for contacting the entire row 20 of reaction vessels 18. However, it is within the scope of this disclosure to provide the movable heaters 27, 28 of each pair of heaters (or all four heaters) in a segmented format for contacting individual reaction vessels 18 independently. Each subsection may be controlled by a separate means for moving.

In the operation of the two-temperature thermal cycling system 10 illustrated, a strip or row 20 of reaction vessels 18 is loaded into the active area of subassembly 12, as shown in FIG. 4A, such that row 20 extends between the upper and lower pairs of heaters 29. To thermal cycle the reaction mixtures 16, the fourth heater 28 is moved to the closed position toward first, stationary heater 25, as shown in FIG. 4B. Moving heater 28 to the closed position causes heater 28 and heater 25 to impinge on the outer walls of the reaction vessels 18 positioned therebetween, thus squeezing substantially all of the reaction mixture 16 to the upper portion of the respective reaction vessel 18. The width of a vessel receptacle gap 35 between second heater 26 and third heater 27, in the opened position, is large enough to allow the mixture 16 to flow into the upper half of the reaction vessel body 19 while still maintaining direct contact with the outer walls of the reaction vessel 18. As shown in FIG. 4C, the width of a vessel receptacle gap 37 between heaters 25 and 28, in the closed position (shown in FIG. 4B), has been opened by moving fourth heater 28 to the opened position in a direction away from first heater 25 while the receptacle gap 35 between heaters 26 and 27 is closed by generally simultaneously moving third heater 27 to the closed position toward second heater 25.

While the illustrated embodiment of the thermocycling subassembly 12 shown in FIGS. 3 and 4A-4C uses the first and fourth heaters 25, 28 positioned within lower zone 68 as the annealing site, those skilled in the art could envision other arrangements. For example, the upper heaters 26, 27 may be used to anneal and the lower heaters 25, 28 may be used to denature the DNA within the reaction mixture 16. Further, as mentioned above, it is within the scope of this disclosure to include a subassembly 12 having more than two sets or zones of heaters for cycling between more than two temperatures. For example, three sets of heaters could produce typical three-temperature PCR profiles with different temperatures used for denaturation, annealing, and extension. An arrangement where the temperature zones are arranged horizontally rather than standing vertically is also envisioned.

One way to accomplish rapid uniform heating and cooling of the reaction mixture 16 is to maintain a small distance between heaters 25 and 28 and between heaters 26 and 27 (or, vessel receptacle gap 35) in the active temperature zone. However, it is also conceivable that rapid temperature uniformity of the reaction mixture 16 can be achieved by agitation of the system 10. Illustratively, for temperature transitions used in two-temperature PCR systems, a vessel receptacle gap 35 of about 0.1 mm to about 2 mm is preferred, with 0.25 to 1 mm being the most preferred, for the active temperature zone when respective heaters are in the opened position for effective heating or cooling of the reaction mixture. When respective heaters are in the closed position, illustratively a vessel receptacle gap 37 is brought as close as possible to the thickness of the fully collapsed sample vessel, illustratively approximately 0.1 to 0.15 mm. Furthermore, illustratively, the speed of closing and opening of the heaters 29 within each respective zone is relatively fast. Again, in the case of two-temperature PCR systems, a closing and opening speed of 5 mm/s to 0.01 mm/s is preferred, with about 1 mm/s being the most preferred. However, it is within the scope of this disclosure for heaters 27, 28 to open and close at other suitable speeds. Further, it is understood that in some applications, slower temperature transitions may be preferred, with concomitant slower closing and opening speeds.

FIGS. 5 and 6 show the integration of the thermocycling subassembly 12 into the real-time PCR detection system 10. As mentioned above, thermocycling subassembly 12 is mounted on support 36 coupled to base 46. Fluorimeter subassembly 38 is mounted below the thermocycling subassembly 12. The fluorimeter subassembly 38 can be moved along a fluorimeter linear bearing 40 by a fluorimeter drive shaft 42. Further, a stepper motor 44 is provided and is computer controlled to turn the fluorimeter drive shaft 42 to move the fluorimeter subassembly 38. FIG. 6 shows the cross section of the composite apparatus. When the lower vessel receptacle gap 35 is open, the fluorimeter subassembly 38 can measure the fluorescence of the reaction mixture 16 within one of the reaction vessels 18. Moving the fluorimeter subassembly 38, as described above, allows monitoring of the individual reaction vessels 18 in a row or strip 20.

Figure 7:
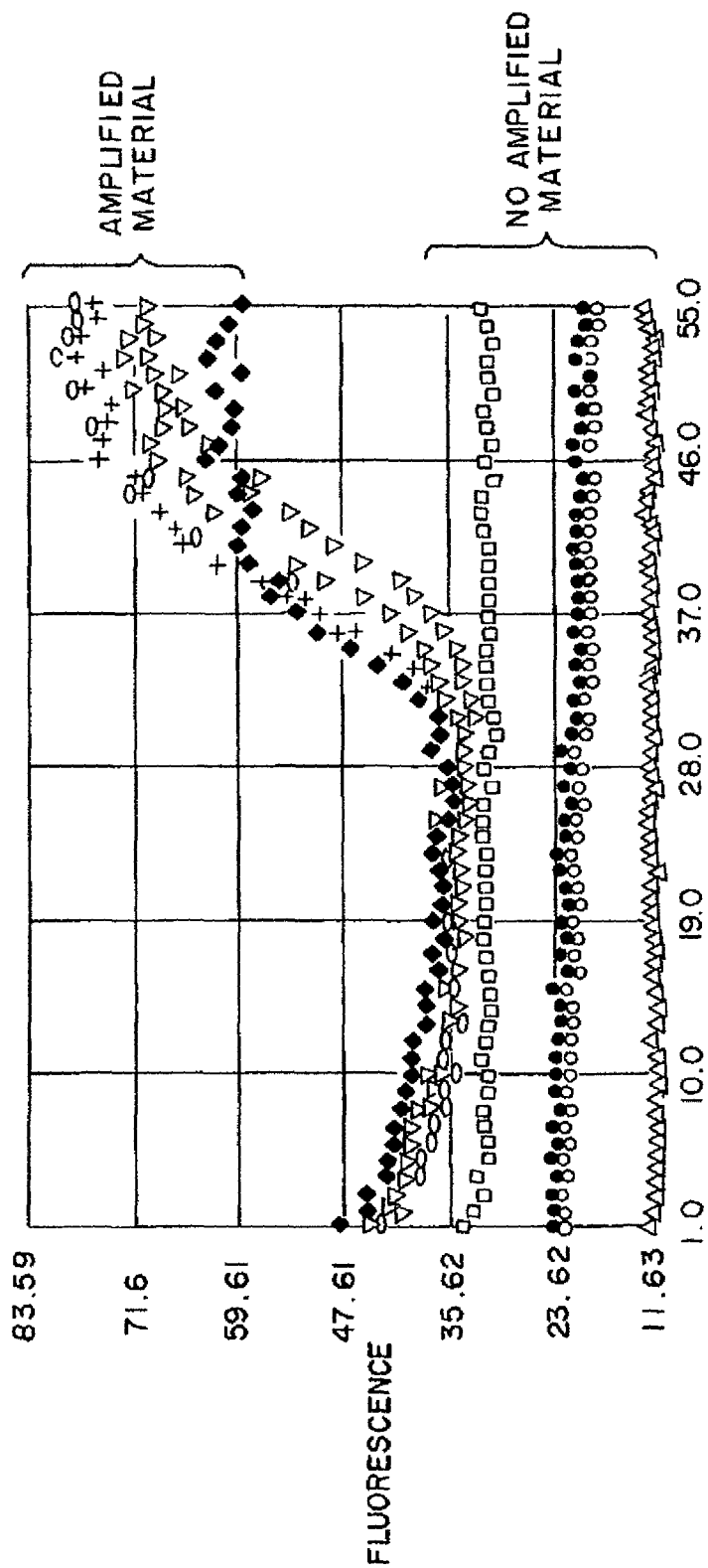
FIG. 7 is a graph showing the results of real-time monitoring of PCR in which DNA amplification is detected by the increase in relative fluorescence in the annealing temperature zone. (Δ, ○, ●, ﺣ are negative controls; ∇, ◯, ◆, + are positive samples)

FIG. 7 illustrates an example of PCR in which a DNA fragment was amplified using the real-time system described in FIGS. 5 and 6. A 110 base pair fragment of the human beta-globin gene was amplified using DNA primers 5'ACA-CAACTGTGTTCACTAGC (SEQ ID NO. 1) and 5' CAACTTCATCCACGTTCACC (SEQ ID NO. 2) at 0.5 µM each, 1×SYBR Green I dye (Molecular Probes, Eugene, Oreg., 1:30,000 dilution), 200 µM dNTPs, 0.04 U/µl Taq polymerase with TaqStart Antibody (Roche Molecular Biochemicals, IN), and PCR buffer (Idaho Technology, UT). Approximately fifteen thousand copies of human genome DNA were included in one hundred microliter reaction mixtures. The reaction mixtures 16 were placed in reaction vessels 18 and were temperature-cycled for 50 cycles with the following temperature profiles: 95° C., 4 seconds, 60° C., 2 seconds. In FIG. 7, amplification of material was confirmed in eight reaction mixtures indicated by the increase in fluorescence after 37 cycles. The identity of the amplified material was confirmed as the beta-globin fragment by comparing its melting temperature with that of a reference material using the LightCycler system (Roche Molecular Biochemicals). In one illustrated embodiment, the PCR reagents could be lyophilized in the reaction vessel and reconstituted by adding sample dissolved in water.

Figure 8:
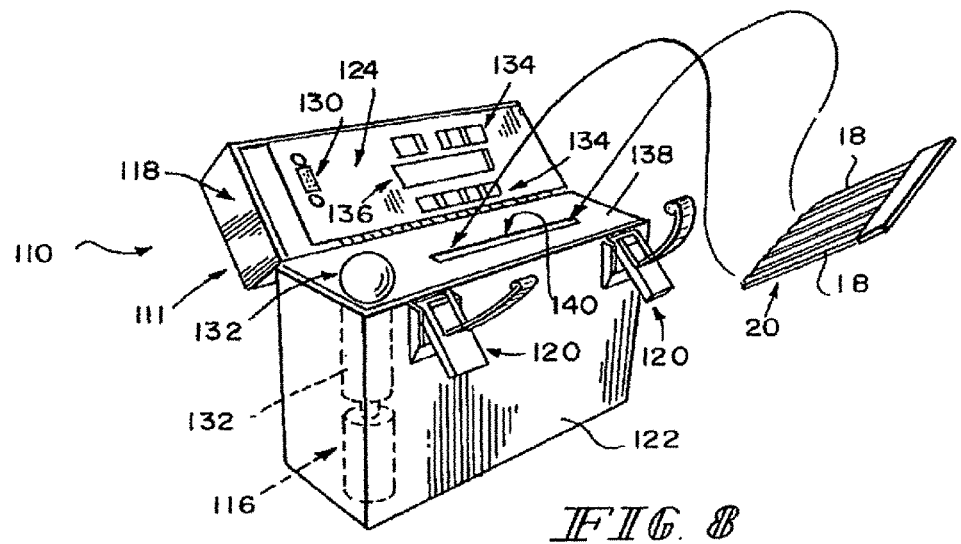
FIG. 8 is a perspective view of an alternative real-time PCR apparatus showing a body of the apparatus including a slot for placing sample vessels therein and a pressurized gas chamber adjacent the slot, and showing the apparatus further including a lid hinged to the body and including a computer having a PC interface and display monitor.

Looking now to FIGS. 8 and 9, an alternative PCR apparatus 110 is provided. Apparatus 110 is similar to apparatus 10 and, therefore, like reference numbers have been used to identify like components. Apparatus 110 also performs the same functions as apparatus 10 such as temperature cycling and detection and analysis of a reaction mixture. Apparatus 110 performs these functions through the use of a thermocycling subassembly 112 and a fluorimeter subassembly 114. One difference between apparatus 10 and apparatus 110 is that the movable heaters 27, 28 of apparatus 110 are operated by two sets of pneumatic bladders 129, 131. Although illustrative pneumatic bladders are disclosed, it is within the scope of this disclosure to move heaters 27, 28 through the use of any suitable pressure-based actuator such as hydraulics, spring arrays, etc., for example.

The first, upper set 129 of bladders includes upper bladders 144, 146 coupled to movable heater 27 and the second, lower set 131 of bladders includes lower bladders 148, 150 coupled to movable heater 28. Bladders 144, 146, 148, 150 are each illustratively manufactured by heat-sealing a polyethylene/polypropylene laminate film onto a pneumatic fitting 128. The seals are arranged such that rounded, rectangular areas are created and positioned adjacent the heaters. Illustratively, each bladder 144, 146, 148, 150 (and each respective heater 25, 26, 27, 28 coupled thereto) generally runs the length of apparatus 110 so that each bladder 144, 146, 148, 150 affects all vessels 18 within the array 20 of vessels 18. Further each bladder 144, 146, 148, 150 is illustratively coupled to two pneumatic fittings 128, although only one fitting 128 is shown in cross-section in FIG. 9.

In operation, air is forced into the fittings 128 to inflate each plastic film bladder 144, 146, 148, 150 thus forcing the heater elements 60 coupled to each movable heater 27, 28 into contact with vessels 18 and respective heater elements 60 of stationary heaters 25, 26 to force the liquid sample 16 within each vessel 18 into the other heating zone. Apparatus 110 may include a rigid mechanical support 126 coupled to each set 129, 131 of bladders and an insulator 133 coupled to each support 126. Illustratively, mechanical support 126 is made of a metal or carbon fiber composite strips, however, it is within the scope of this disclosure for support 126 to be made of any suitable material. As shown, one insulator 133 is coupled to heater 27 and another insulator 133 is coupled to heater 28. Each insulator 133 is made of an insulating material so that the temperature of each respective heater 27, 28 may be more consistently maintained.

As shown in FIG. 9, each movable heater 27, 28 is coupled to two bladders. Illustratively, heater 27 is coupled to the first, upper set 129 of bladders 144, 146 and heater 28 is coupled to the second, lower set 131 of bladders 148, 150. The use of two bladders for each movable heater 27, 28 allows for active mixing of the samples 16 within each of the upper and lower heat zones 66, 68. Agitation of the samples 16 is accomplished by cyclically pressurizing bladders 144 and 146 (of upper set 129) within upper zone 66, for example, or by cyclically pressurizing bladders 148 and 150 (of lower set 131) within lower zone 68. Subminiature valves (not shown) under control of a microprocessor 162 (shown diagrammatically in FIG. 9) may be used to switch the high pressure between the two heat zones 66, 68 thus forcing the sample 16 back and forth between the upper and lower temperature zones 66, 68. Illustratively, all pneumatic bladders 144, 146, 148, 150 are controlled by microprocessor 160. Further, illustratively, a separate microprocessor is used to control temperature sensing, the heating of the heater elements 60, etc.

As shown in FIG. 9, apparatus 110 further includes a sealing mechanism 142 driven by another bladder 152. Sealing mechanism 142 includes a spring-retracted seal bar 156 coupled to bladder 152. To seal the samples 16 into the vessels 18, bladder 152 is inflated to actuate spring-retracted seal bar 156 to press seal bar 156 into contact with the array 20 of vessels 18 and between a mating surface 158 of seal bar 156 and an opposite surface 160 of apparatus 110. Mating surface 158 of seal bar 156 is illustratively fitted with a nichrome wire (not shown), which can be heated by passing current therethrough. The wire is heated for enough time to melt an inner layer of the reaction vessel body 19, fusing it together and locking the sample 16 into the receptacle. While sealing mechanism 142 is provided integrally in apparatus 110, it is understood that sealing mechanism 142 is optional, and that the vessels 18 may be sealed by any number of ways, as is known in the art.

A controller board (not shown) is also provided and includes a heater board retraction spring, MAC valves, and receptacles for fittings 128. Apparatus 110 is illustratively battery operated and includes an internal pneumatic system, described above, including first and second sets 129, 131 bladders 144, 146 and 148, 150. Illustratively, first set 129 of bladders 144, 146 acts as a first mover or actuator of the system and second set 131 of bladders 144, 146 acts as a second mover or actuator of the system. A disposable twenty-five gram carbon dioxide cylinder 132 is illustratively used to drive the pneumatic system. While FIGS. 8 and 9 illustrate a portable, battery operated unit, it is understood that apparatus 110 may be configured to run off of a standard electrical source. Furthermore, while a carbon dioxide cylinder 132 is illustrated, it is understood that other compressed fluid sources may be used within the scope of this disclosure.

As shown in FIG. 8, apparatus 110 includes a transport box 111 having a body 116 and a lid 118 illustratively coupled to the body 116 by hinges (not shown) so that lid 118 pivots between an opened position, as shown, and a closed position. Illustratively, box 111 is made of sturdy anodized aluminum, however, it is within the scope of this disclosure to include a transport box made of other suitable materials. Latches 120 are coupled to a front surface 122 of body 116 so that lid 118 may be locked in the closed position and the transport box may be easily carried. Lid 118 illustratively includes a 386 DOS computer 124, however, any suitable computer or microprocessor may be used. A PC interface 130 is provided so that computer 124 may be connected to a user's PC to download information gathered from the apparatus 110 to the PC. An interface 134, illustratively a soft key interface, is provided including keys for inputting information and variables such as temperatures, cycle times, etc. Illustratively, a 2×20 mm character display 136 is also provided. Display 136 may be an LED, LCD, or other such display, for example. Further as shown in FIG. 8, body 116 of box 111 includes a top surface 138 having a slot 140 formed therein for receiving array 20 of vessels 18. It is understood that other microprocessors may be used within the scope of this invention. It is further understood that the microprocessor need not be provided as an integral component of the apparatus 110, and, depending upon the application, that a microprocessor may not be needed at all.

Illustrative automatic calling software may be provided to analyze the samples by a multi-test analysis method described in U.S. patent application Ser. Nos. 10/074,178 and 10/117,948, herein incorporated by reference, with the following modifications and additions. Multiple points (for example, 10, 20, 30, or 50 points) are interrogated across a bottom 15 of each individual sample vessel 18 to acquire multiple fluorescence values, and the median of those fluorescence values for each time point is used as input to the algorithm. Data points from portions of the sample vessel 18 that are close to seal 22 are preferably not used due to edge effects in fluorescence. Prior to taking the median, the software also compares the individual fluorescence values with data acquired from the cycle preceding the present acquisition, and ignores those values that are significantly different in value. This allows the software to ignore portions of the sample vessel 18 which further generate erroneous fluorescence signal due to the appearance, or drift, of air bubbles and other interfering particles in the reaction. It is understood that other numerical methods besides taking a median value may be sued to reduce the many measurements taken across the bottom to a single fluorescence value for each sample. These include Fourier transformation, averaging, fitting to known functions, and stored standards. Finally, in an illustrated embodiment, the classification of a sample (i.e. "positive" or "negative" for the presence of an analyte) is reported to the user only if the automated calls have registered the expected results in the positive and negative controls, and optionally, only if duplicate reactions or alternative gene loci provide concordant results with the sample. Illustratively, if the automated calls are inconsistent with the expected calls in the positive and/or negative controls, then the software will report to the user that the reaction needs to be repeated. If the result of the duplicate reaction, or the alternative gene loci, is inconsistent with the sample, the software will report the inconsistency and will not call the sample "positive" or "negative". Apparatus 110 displays the result in the display screen 136 and allows users to look deeper at the specific reactions if they choose.

As mentioned above, apparatus 110 further includes gas chamber 132 for providing compressed gas to the first and second sets 129, 131 of pneumatic bladders 144, 146, 148, 150. As shown in FIG. 8, cylinder 132 is positioned near slot 140 so that a portion of chamber 132 protrudes above top surface 138 of body 116. Chamber 132 is removable from body 116 of transport box 111 so that a user may refill the chamber 132 as needed. Although chamber 132 is illustratively cylindrical in shape, it is within the scope of this disclosure to include a gas chamber having any suitable shape for feeding compressed air to bladders 129, 131. Similar to apparatus 10, apparatus 110 includes thermocycling subassembly 112 and fluorimeter subassembly 114, each positioned within body 116 of transport box 111. Computer 124 of apparatus 110 may control certain functions of both subassemblies 112, 114. It is also within the scope of this disclosure, however, to include other computers or microprocessors for separately controlling the subassemblies 112, 114.

Looking now to FIG. 9, thermocycling subassembly 112 includes heaters 25, 26, 27, 28 to create upper and lower temperature zones 66, 68. Further, heaters 25 and 26 are stationary heaters and heaters 27 and 28 are movable heaters. As mentioned before, first, upper set 129 of pneumatic bladders 144, 146 is coupled to heater 27 and second, lower set 131 of pneumatic bladders 148, 150 is coupled to heater 28. Although it is shown that two bladders are coupled to each heater, it is within the scope of this disclosure to couple a heater to any suitable number of pneumatic bladders. Each bladder 144, 146, 148, 150 is coupled to the carbon dioxide chamber 132. Microprocessor 160 controls the inflation and deflation of each set 129, 131 of bladders 144, 146, 148, 150 as is required for the temperature cycling process described above with respect to apparatus 10. Pneumatic bladders 144, 146, 148, 150 provide high, uniform actuation forces on respective heaters 27, 28. Further, illustrative bladders 144, 146, 148, 150 are relatively light and occupy little space allowing for apparatus 110 to be small, compact, and portable.

Subassembly 112 also includes an eleven-valve manifold coupled to the bladders 144, 146, 148, 150 to regulate the carbon dioxide gas into and out of each bladder 144, 146, 148, 150. Although an eleven-valve manifold is disclosed herein, it is within the scope of this disclosure to include a manifold having another suitable number of valves to operate bladders 144, 146, 148, 150. The carbon dioxide gas within gas chamber 132 is regulated to 30 psi and is switched through the manifold to minimize electrical losses from the valves. First set 129 of pneumatic bladders 144, 146 forces movable heater 27 toward stationary heater 25 while second set 131 of pneumatic bladders 148, 150 forces movable heater 28 toward stationary heater 26 in order to force samples 16 within each vessel 18 between lower and upper temperature zones 66, 68.

In operation, the illustrative sets 129, 130 of bladders 144, 146 and 148, 150 are able to produce a rocking motion on respective movable heaters 27 and 28 to allow mechanical mixing of the samples 16 within each temperature zone 66, 68. Mixing the samples 16 by the rocking motion of the heaters 27, 28 increases temperature uniformity within each sample 16 and aids in positioning each sample 16 for optimal fluorescence measurement at the bottom of each respective vessel body 19.

Subassembly 112 further includes a sealing mechanism 142, shown in FIG. 9 and described above, positioned above heaters 26, 27. Array 20 of vessels 18 are inserted into slot 140 of body 116 and between mating surface 158 of seal bar 156 and surface 160. Seal bar 156 is urged to move toward surface 160 by pneumatic bladder 152 to lock and seal the array 20 of vessels 18 therebetween, as described above. Illustratively, seal bar 156 operates to heat seal an upper portion of the vessel body 19 of each vessel 18 together to form a seal. However, it is within the scope of this disclosure for seal bar 156 to simply clamp or secure array 20 of vessels 18 between stationary heaters 25, 26 and movable heaters 27, 28.

The foregoing description of the invention has been presented for purposes of illustration and description. It is not intended to be exhaustive or to limit the invention to the precise forms described, and obviously many other modifications are possible in light of the above teaching. The embodiments were chosen in order to explain most clearly the principles of the invention and its practical applications, thereby to enable others in the art to utilize most effectively the invention in various other embodiments and with various other modifications as may be suited to the particular use contemplated.

What is claimed is:

1. A method for amplifying a nucleic acid in a biological sample comprising:
   (a) placing the biological sample into a flexible reaction vessel comprising a first region and a second region adjacent to and in fluid communication with the first region,
   (b) compressing the first region to force the sample into the second region and into contact with a pair of denaturation heaters at a denaturation temperature,
   (c) compressing the second region to force the sample into the first region and into contact with a pair of annealing heaters at an annealing temperature, and
   (d) repeating steps (b) and (c) for a plurality of amplification cycles,
   wherein the flexible reaction vessel comprises a plurality of individual reaction vessels coupled together to form a row of reaction vessels.

2. The method of claim 1 wherein the flexible reaction vessel further comprises a fitment having a channel fluidly connected to at least a portion of the individual reaction vessels, the fitment further having a port for receiving the reaction mixture prior to step (a), the port fluidly connected to the channel.

3. The method of claim 1 wherein the nucleic acid is amplified by PCR and the sample vessel further comprises therein reagents for performing PCR.

4. The method of claim 3 wherein the reagents include a polymerase and primers.

5. The method of claim 4 wherein the reaction vessel further comprises a fluorescent entity therein, the fluorescent entity capable of providing a fluorescent signal related to the quantity of the nucleic acid.

6. The method of claim 5 comprising monitoring the fluorescent signal during each of the amplification cycles.

7. The method of claim 6 further comprising using the fluorescent signal to call a positive or negative result.

8. The method of claim 7 further comprising comparing the positive or negative result to a second result obtained for a second sample and outputting the result only if the result and the second result are in agreement.

9. The method of claim 7 further comprising obtaining an additional result for a positive or negative control and outputting the result for the sample only if the additional result is correct for the positive or negative control.

10. A method for repeatedly heating and cooling a reaction mixture contained within a flexible reaction vessel comprising:
    (a) placing the reaction vessel adjacent a first heater and a second heater,
    (b) heating the first heater to a first temperature,
    (c) heating the second heater to a second temperature, and
    (d) alternately opening and closing the first and second heaters so that the reaction mixture is in thermal contact with the respective heater when the heater is in the opened position and the reaction mixture is not in thermal contact with the respective heater when the heater is in the closed position,
    wherein the flexible reaction vessel comprises a plurality of individual reaction vessels coupled together to form a row of reaction vessels.

11. The method of claim 10, wherein opening and closing includes moving the first heater to a closed position to move substantially all of the reaction mixture to a position adjacent the second heater, heating the reaction mixture to the second temperature, moving the first pair of heaters to an opened position and moving the second pair of heaters to a closed position to move substantially all of the reaction mixture to a position adjacent the first pair of heaters, and heating the reaction mixture to the first temperature.

12. The method of claim 10 wherein the flexible reaction vessel further comprises a fitment having a channel fluidly connected to at least a portion of the individual reaction vessels, the fitment further having a port for receiving the reaction mixture prior to step (a), the port fluidly connected to the channel.

13. A method for heating a reaction mixture heating and cooling a reaction mixture contained within a flexible reaction vessel comprising:
heating a first pair of heaters positioned in a first zone to a first temperature,
heating a second pair of heaters positioned in a second zone to a second temperature,
placing the reaction vessel between each of the first and second pair of heaters so that the first heater engages a first portion of the reaction vessel and the second heater engages a second portion of the reaction vessel, and
moving the reaction mixture between the first zone in thermal contact with the first pair of heaters and the second zone in thermal contact with the second pair of heaters by alternately opening and closing the first and second pairs of heaters around the reaction vessel,
wherein the flexible reaction vessel comprises a plurality of individual reaction vessels coupled together to form a row of reaction vessels.

\* \* \* \* \*